United States Patent [19]

Jankelson et al.

[11] 4,174,706

[45] Nov. 20, 1979

[54] MANDIBLE STIMULATOR

[75] Inventors: Bernard Jankelson, 1451 Medical-Dental Bldg., Seattle, Wash. 98101; John C. Radke, Seattle, Wash.

[73] Assignee: Bernard Jankelson, Seattle, Wash.

[21] Appl. No.: 810,507

[22] Filed: Jun. 27, 1977

[51] Int. Cl.² .......................... A61B 5/05; A61N 1/36
[52] U.S. Cl. .................................. 128/741; 128/791; 128/422
[58] Field of Search .................... 128/422, 410, 419 R, 128/421, 423, 2.1 R, 2.1 P, 2.1 Z, 2.06 R, 1 C

[56] References Cited

U.S. PATENT DOCUMENTS

| | | | |
|---|---|---|---|
| 2,771,554 | 11/1956 | Gratzl | 128/421 |
| 3,160,159 | 12/1964 | Hoody et al. | 128/1 C X |
| 3,548,807 | 12/1970 | Crovella | 128/2.06 R |
| 3,648,708 | 3/1972 | Haeri | 128/422 |
| 3,797,500 | 3/1974 | Porter | 128/422 |
| 3,897,789 | 8/1975 | Blanchard | 128/422 X |
| 3,902,502 | 9/1975 | Liss et al. | 128/422 |
| 3,989,051 | 11/1976 | Nozhnikov et al. | 128/421 |
| 4,027,663 | 6/1977 | Fischler et al. | 128/2.06 R |

*Primary Examiner*—Lee S. Cohen
*Attorney, Agent, or Firm*—Seed, Berry, Vernon & Baynham

[57] ABSTRACT

A stimulator for causing involuntary mandibular closure. In a "test" mode a constant voltage is applied to left and right electrode circuits, and the currents through the electrode circuits are measured to determine electrode circuit conductivity. A first comparator circuit flashes respective "open" circuit warning lamps if the current through either of the electrodes is less than a preset value, and it flashes a "good" connection indicator lamp if the current through both electrodes is greater than the preset value. A second comparator circuit determines if the current through one electrode exceeds the current through the other electrode by a preset value, and flashes respective "low" current warning lamps in response thereto. In the "pulse" mode an oscillator repetatively charges a capacitor to a high voltage through a pulse transformer, and the high voltage is then gated to a control circuit which generates a current pulse having an adjustable amplitude through the electrode circuits to produce involuntary mandibular closure. The amplitude of the current through one electrode circuit with respect to the current through the other electrode circuit may be adjusted with a balance control. In the "pulse" mode, the battery voltage is also measured, and respective lamps flash in synchronism with the current pulses to indicate whether the battery is producing the proper voltage or whether the battery must be replaced.

7 Claims, 3 Drawing Figures

MANDIBLE STIMULATOR

BACKGROUND OF THE INVENTION

1. Field of the Invention

This invention relates to mandible stimulators, and, more particularly, to a mandible stimulator for producing current pulses through one or more electrode circuits having an optimum duration and an amplitude which is directly proportional to the rotational position of a potentiometer, and which includes a self-test system for flashing appropriate indicator lamps responsive to open circuit, circuit unbalance and low battery conditions.

2. Description of the Prior Art

The stimulation of muscles in the human body by electrical stimuli to provide involuntary muscular response has become a useful remedial, diagnostic and clinical technique; and in some instances, as with a cardiac stimulator, electrical stimulation has been substituted for normal electrochemical nerve signals. However, the direct, repetitive electrical stimulation of muscles by evenly timed electrical pulses fed from a simple oscillator to a single electrode pair is not practical in some instances where electronic stimulation is required. For example, in techniques producing involuntary mandibular closure, it is clinically important that contraction of the nerve fibers be effected through the motor nerves rather than by controlling the mandible by the individual stimulation of the muscles per se. Direct stimulation of the muscles is impractical due to the number of electrodes which would be required, and stimulation of the motor nerves ensures stimulation of the entire muscle complex. Also, it requires from six to eight times less electrical energy to effectively stimulate the motor nerves than would be required for direct muscle stimulation.

In the electrical stimulation of the motor nerves controlling the masticatory and facial muscles, muscularly balanced closure of the mandible may be achieved by simultaneously and evenly stimulating the motor roots of the mandibular and facial nerves on both sides of the face. If only one muscle group on one side of the face contracts, the mandible will deviate to that side as it closes. Thus, for smooth physiologic closure to occlusion, the entire muscle complex of each side of the face must contract simultaneously in group action.

If simultaneous and bilateral stimulation to produce group action of all the masticatory and facial muscles can be achieved, a number of clinical and diagnostic techniques are possible. For example, controlled stimulation may be employed to diagnose the comparative degree of relaxation or contracture of the muscle groups on each side of the face; to cause the mandible to close to the horizontal myocentric position of occlusion; to determine the vertical position of occlusion; to take denture impressions; to relax muscle spasms associated with Temporomandibular Joint Syndrome; and to reduce post-operative swelling and discoloration by causing gentle massage as the muscles contract.

One mandible stimulator which has been commonly used to perform the above described functions is disclosed in U.S. Pat. No. 3,797,500 assigned to Dr. Bernard Jankelson. Although this apparatus performs adequately under most conditions, the inventive mandible stimulator described herein includes a number of features which result in improved operating and performance characteristics. One disadvantage of this conventional mandible stimulator is that the output of the stimulator is a pulse having a manually adjustable voltage so that the currents through the electrode circuits vary depending upon such variables as the skin resistance of an individual. Since the amount of stimulus provided to the motor nerves depends upon the amount of current in the electrode circuit, and not the voltage, the amount of stimulus provided at a given stimulus setting varies greatly between individuals. Additionally, the relatively long duration pulses of the conventional mandible stimulator may produce undesirable direct stimulation of the muscles. It is generally desirable that the electrical stimuli to both left and right nerves of an individual produce equal muscle response. However, the muscles of one side may be in spasm or contracture and may require a greater stimulus amplitude for an equal balanced muscle response. A balance control is provided so the operator can make the required adjustment. In the stimulator described in U.S. Pat. No. 3,797,500 this is accomplished by separately measuring the current through each electrode circuit with a meter, a procedure which is somewhat time consuming and which may introduce inaccuracies in the measurements. In summary, although the mandible stimulator described in U.S. Pat. No. 3,797,500 can be advantageously used, additional refinements described and claimed herein greatly improve the operating efficiency and accuracy of such devices.

SUMMARY OF THE INVENTION

It is an object of the invention to provide a mandible stimulator which produces electrical stimuli having an intensity corresponding to a manually adjusted setting and which is not affected by operational variables such as skin resistance.

It is another object of the invention to provide electrical stimuli which is a linear function of the rotational position of a potentiometer.

It is still another object of the invention to provide an electrical stimulus having a duration adapted to produce involuntary mandibular closure without causing any direct muscle stimulation.

It is a further object of the invention to provide a mandible stimulator including self-test features which provide visual indications of operational performance that can be easily and quickly interpreted.

These and other object of the invention are accomplished by a mandible stimulator having current source outputs so that the electrical stimuli to mandibular motor nerves is unaffected by operational variables such as skin resistance and skin/electrode interface resistance. The intensity of the electrical stimulus is determined by a pulse amplitude control circuit which includes means for compensating for circuit non-linearities so that the amplitude of the current through the electrode circuit is a linear function of the rotational position of a potentiometer. The electrical stimulus is in the form of a pulse having a duration of approximately 0.5 milliseconds which ensures that the stimuli causing the muscle contraction are being transmitted to the muscles via the 5th and 7th cranial nerves thus ensuring balanced group function rather than individual muscle stimulation. Stimuli with pulse width less than 1 millisecond are effective for neural transmission but not for direct muscle stimulation. The stimuli are effective to cause involuntary mandibular closure. The periodicity of the pulses provides a rest period of 1½ seconds between pulses to ensure that the procedure can be carried on indefinitely without fatigue. The mandible stimulator also includes output current and voltage limiters as safety features to prevent any possibility of excessively inadvertent signals reaching the electrodes. A self-test system in the stimulator monitors the resistance in right and left electrode circuits, and flashes appropriate warning lamps to indicate open circuit and circuit unbalanced conditions in the electrode circuits and to provide an indication of low battery voltage.

DETAILED DESCRIPTION OF THE PREFERRED EMBODIMENTS

Figure 1:
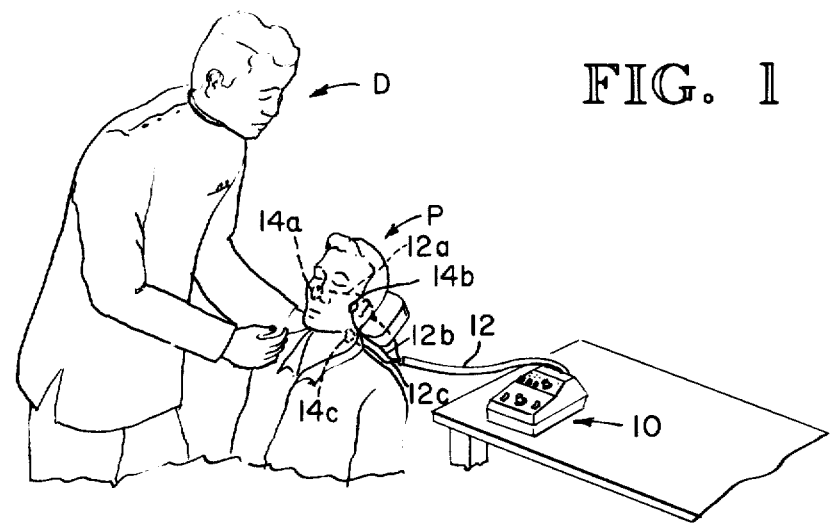
FIG. 1 is an isometric view illustrating the mandible stimulator in use.

As illustrated in FIG. 1, the mandible stimulator 10 is connected to a patient P by the practitioner D through a cable 12. The cable 12 includes three conductors 12a, b, c two of which 12a, b are connected to respective electrodes 14a, b placed on the right and left sides of the face of the patient P. The third conductor 12c is connected to a common dispersal electrode 14c placed along the patient's spine. In order for the electrodes 14 to function properly, they must intimately contact the skin of the patient. However, the resistance between each conductor 12 and the patient P varies depending upon such variables as the characteristics of the electrode, the skin resistance of the patient and the electrode/skin interface characteristics. Consequently, a constant voltage placed on the conductors 12 would provide greatly varying degrees of electrical stimulus to the patient P.

Figure 2:
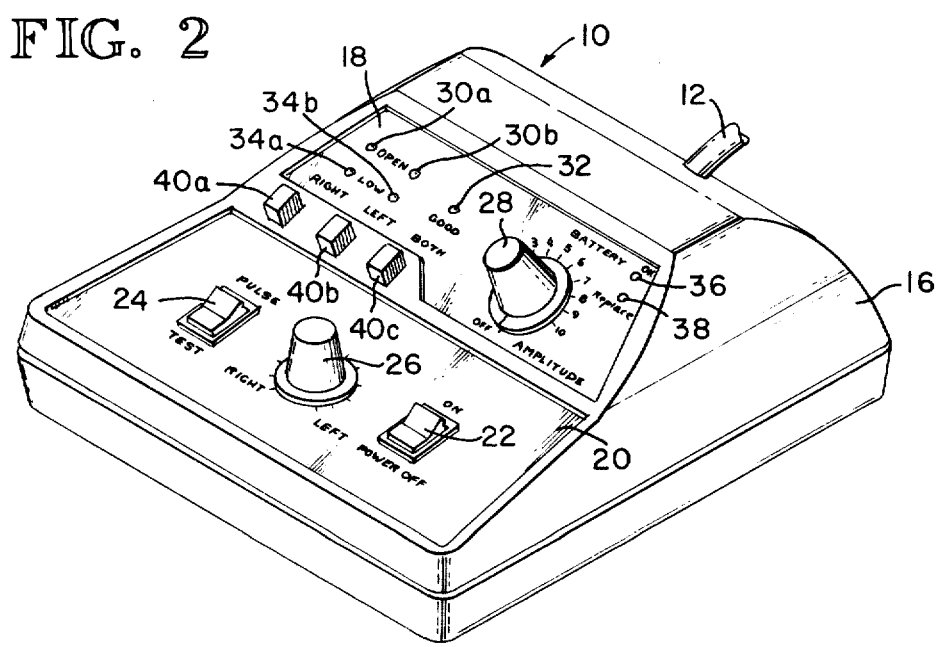
FIG. 2 is an external isometric view of the mandible stimulator.

The external structure of the mandible stimulator 10 as illustrated in FIG. 2 includes a molded plastic case 16 of a pleasing design having an upper control and display panel 18 and lower control panel 20. The lower control panel 20 includes a power switch 22 for switching an internal battery (not shown) to the stimulator circuits and a mode switch 24 for placing the stimulator in either a "pulse" or "test" mode. The lower panel 20 also includes a balance control 26 for controlling the intensity of the electrical stimulus to the right electrode 14a with respect to the intensity of the electrical stimulus to the left electrode 14b. In operation the balance control 26 may be adjusted so that the electrical stimulus to both electrodes 14a, b are approximately equal or to produce unbalanced mandibular closure. The upper display and control panel 18 includes an amplitude control 28 for manually adjusting the intensity of the electrical stimulus between a zero level and a predetermined maximum level. The lefthand side of the panel 18 includes a number of lamps for providing a visual indication of operating conditions when the mode switch 24 is in its test position. The upper pair of lamps 30a, b flash responsive to the resistance through the right and left electrode circuits being above a predetermined magnitude thereby indicating an open circuit condition. Two of the lower lamps 34a, b are utilized to signal an unbalanced condition in which the conductance of one electrode circuit varies from the conductance of the other electrode circuit by a predetermined value. In operation the lamp 34a flashes to indicate that the conductance of the right electrode circuit is low compared to the conductance of the left electrode circuit, and the lamp 34b flashes to indicate that the conductance of the left electrode circuit is low compared to the conductance of the right electrode circuit. If neither of the electrode circuits have a resistance greater than the predetermined maximum so that neither of the lamps 30 are illuminated the rightmost lamp 32 flashes to indicate good circuit connections.

The upper righthand corner of the display and control panel 18 includes a pair of lamps for providing a visual indication of battery condition when the mode switch 24 is in its pulse condition. The upper lamp 36 flashes in synchronism with the electrical stimulus pulses when the battery voltage exceeds a predetermined value, and the lower lamp 38 flashes in synchronism with the electrical stimulus pulses when the battery voltage is less than a predetermined value.

The stimulator 10 also includes three push-button function switches 40 positioned between the panels 18, 20. In their outer position the push-buttons 40a, b connect the output circuits of the stimulator to conductors 12a, b, respectively when the push-button 40c is also in its outer position. The push-buttons 40a, b, c are interconnected so that the push-button switches 40a, b are reset to their outer position by momentarily depressing push-button switch 40c. When push-button 40c is depressed, both electrode circuits are open.

In operation the mandible stimulator 10 is connected to the patient P by the practitioner D as illustrated in FIG. 1. The amplitude control is then rotated to its counterclockwise or "off" position, the mode switch 24 is placed in its test position and the power switch 22 is placed in its "on" position. The stimulator 10 then measures the resistance through the electrode circuits and illuminates open circuit indicator lamps 30a, b in the event that the right or left electrode circuits, respectively, have a resistance exceeding a predetermined value which might be caused by a failure to connect the electrode leads 12 to the electrodes 14. Alternatively, the lamp 32 flashes to indicate a good connection. The practitioner D will also observe whether either of the low conductance indicator lamps 34a, b are flashing, which might be caused by a failure to place a layer of conductive gel on one of both of the electrodes 14. All of the switches 40 are normally in their outer position during the "test" mode so that both electrode circuits are closed. The mode switch 24 is then placed in its "pulse" position and the amplitude control 28 is rotated clockwise until the proper intensity of electrical stimulus is being applied to the electrodes 14. During this time the practitioner D will observe the indicator lights 36, 38 to insure that the battery voltage is sufficient for normal operation. If desired the balance control 26 may be adjusted to produce unsymmetrical or unbalanced mandibular closure. Since the lamp 36 flashes in synchronism with the electrical stimulus pulses it is possible for the practitioner D to apply a single pulse to either or both electrodes 14 by depressing the "both" push-button switch 40c and then placing it in its outer position for one flash of the lamp 36 before returning the switch 40c to its depressed position. Since the mandible stimulator can be adjusted and its proper operation verified simply by observing the condition of a relatively few lamps involunary mandibular closure can be easily and quickly produced without resorting to difficult and potentially inaccurate reading and interpretation of meters.

Figure 3:
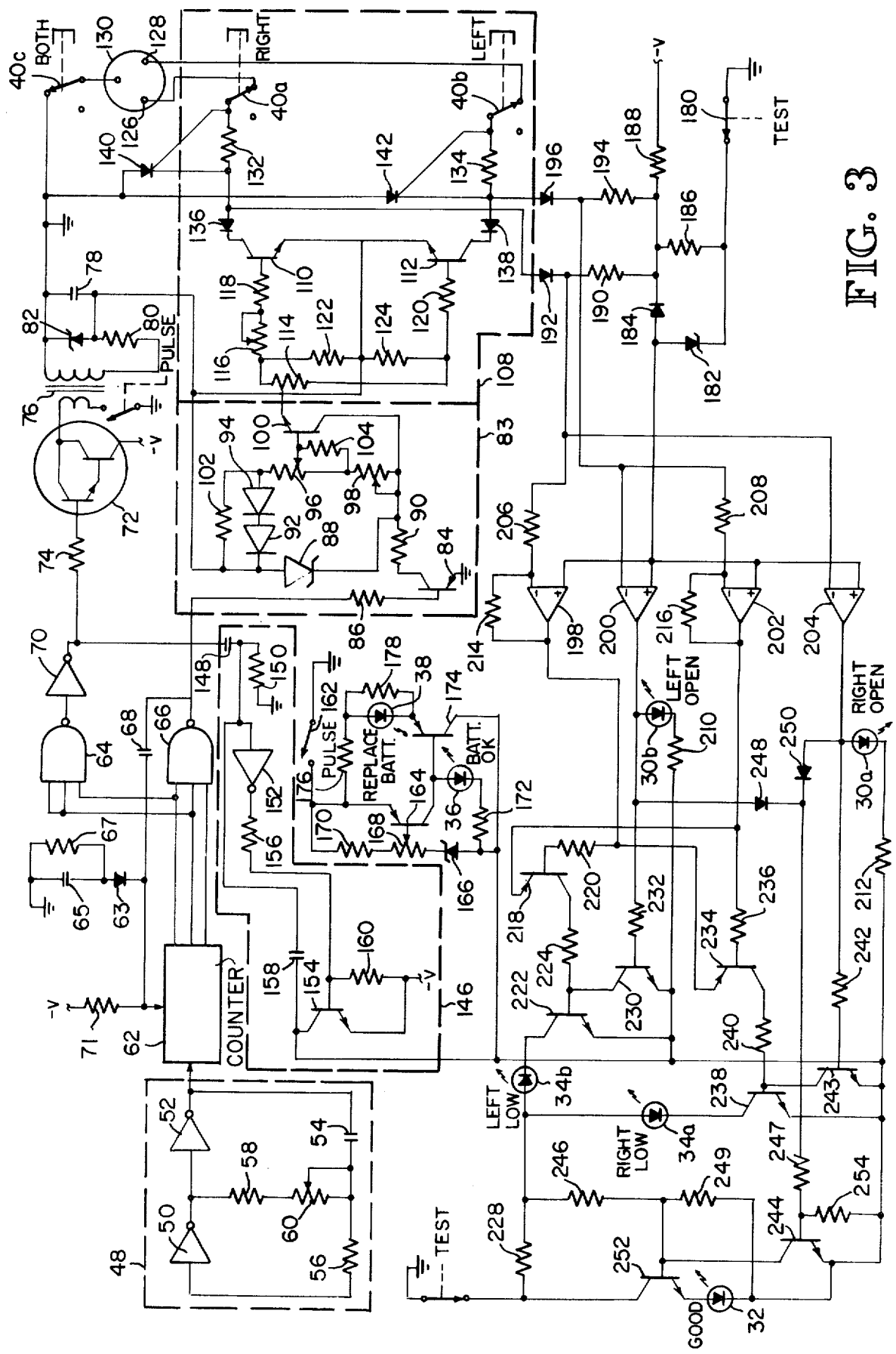
FIG. 3 is a schematic of the mandible stimulator circuits.

A schematic for the mandible stimulator is illustrated in FIG. 3. The basic timing for the stimulator is provided by an oscillator circuit 48 including a pair of inverters 50, 52. As inverter 52 switches from logic "0" to logic "1" ("0" being approximately equal to $-V$ and "1" being approximately equal to ground potential) capacitor 54 begins charging in the opposite polarity so that the voltage on the left side of capacitor 54 is a negative going positive voltage. Capacitor 54 then continues to discharge through resistors 56, 58 and 60. The rate of discharge may be adjusted by adjusting the position of the wiper on potentiometer 60. When capacitor 54 has been discharged to the point where the input of inverter 50 reaches the transfer or switching voltage the voltage level the output of inverter 50 switches to "1" causing the output of inverter 52 to fall to "0". The "1" to "0" transition at the output of inverter 52 drives the left lead of capacitor 54 to below $-V$. Capacitor 54 then discharges in the opposite direction through resistors 56, 58 and 60 until the input to inverter 50 reaches the transfer of switching voltage at which time both of the inverters 50, 52 reverse state. Although the operating frequency of the oscillator is not critical, in one operational embodiment potentiometer 60 is adjusted so that the output frequency is 2024 $H_z$.

The output of inverter 52 increments a 12 stage binary counter 62 having its 3072 count detected by NAND gate 64 and its 3073 count detected by NAND gate 66. For an oscillator frequency of 2024 $H_z$ the 3072 count is reached approximately every 1.5 seconds and the duration of each count is approximately 0.5 milliseconds. Consequently, the output of NAND gate 64 falls to "0" approximately every 1.5 seconds, and the output of NAND gate 66 falls to "0" approximately 0.5 milliseconds after the output of NAND gate 64. On the 3074 count of counter 62 the output of NAND gate 66 switches to "1" and this transition is coupled through capacitor 68 to the reset terminal of counter 62. The reset terminal of counter 62 is normally held in its logic "0" condition by a negative voltage supplied through resistor 71. However the "0" to "1" transition at the output of NAND gate 66 produces a positive going pulse on the reset terminal which resets the counter 62 to zero and causes the output of NAND gate 64 to switch from "0" to "1". The reset terminal of counter 62 is also connected to ground through a diode 63 and a parallel combination of capacitor 65 and resistor 67. This circuit holds the reset terminal at logic "1" for a short period after power is applied to reset the counter 62. In summary, approximately every 1.5 seconds a negative going pulse is produced at the output of NAND gate 64, approximately 0.5 milliseconds later a negative going pulse is produced at the output NAND gate 66, and approximately 0.5 milliseconds later both pulses terminate. As explained in greater detail hereinafter, the pulse from the output of NAND gate 64 charges a capacitor to a relatively high voltage so that a stable, relatively high voltage is available 0.5 milliseconds later when the pulse at the output of NAND gate 66 produces an electrical stimulus pulse. The negative going pulse from the output of NAND gate 64 is received by inverter 70 which saturates darlington pair 72 through resistor 74. When the mode switch 24 is in its "pulse" position current then flows through the primary of pulse transformer 76 to produce a relatively high voltage pulse across the secondary of transformer 76. The high voltage pulse then charges capacitor 78 through resistor 80 to 60 volts as determined by zener diode 82 which acts as an output voltage limiter.

The negative going pulse at the output of NAND gate 66 which occurs approximately 0.5 milliseconds after capacitor 78 begins charging responsive to the pulse from the output of NAND gate 64 is applied to a pulse amplitude control circuit 83. The trigger pulse from the output of NAND gate 66 saturates transistor 84 through resistor 86 allowing current to flow through zener diode 88 and resistor 90. Current then flows through diodes 92, 94 and potentiometers 96, 98. Potentiometer 96 is connected to the amplitude control 28, and potentiometer 98 is an internal calibration potentiometer for adjusting the maximum output current. The position of the wiper of potentiometer 98 thus controls the voltage drop across the potentiometer 96, and the position of the wiper of potentiometer 96 determines the voltage applied to the base of buffer transistor 100. Potentiometer 96 has a linear resistance element so that when it receives a constant voltage the voltage on the potentiometer wiper is approximately a linear function of the position of the potentiometer. However, as the wiper for potentiometer 96 moves away from the anode of diode 94 the base currents of transistors 110 and 112 increase somewhat nonlinearly. Consequently, resistors 102, 104 are provided to compensate for the non-linear effects of the increase in base currents of transistors 110 and 112 so that the current outputs of transistors 110 and 112 are a linear function of the position of the wiper of potentiometer 96.

The control signal on the emitter of transistor 100 is applied to the wiper of potentiometer 114 of a balance and output circuit 108 the winding of the potentiometer 114 is connected to transistors 110, 112 through resistors 116, 118 and 120, respectively. Potentiometer 114 is connected to the balance control 26 (FIG. 2) while potentiometer 116 is an internally accessible calibration potentiometer. The wiper of potentiometer 116 is set so that the output currents of transistors 110 and 112 are equal when the wiper of potentiometer 114 is in its center position. When the wiper of potentiometer 96 is moved all the way toward the anode of diode 94 the diodes 92, 94 are placed in parallel with the base-emitter junction of transistor 100, a combination of resistors and potentiometers 114–120 and a parallel combination of the base-emitter junctions of transistors 110, 112. Consequently, the voltage drop across diodes 92, 94 is equal to the voltage drop across the base-emitter junctions of transistors 100, 110, 112 so that the transistors 100, 110, 112 are cut off just at the point of conduction. The diodes 92, 94 also provide temperature compensation for the transistors 100, 110, 112 since any variations in the base-emitter characteristics of the transistors 100, 110, 112 are compensated for by the variations in characteristics of the diodes 92, 94. When the wiper of potentiometer 96 is moved away from the anode of diode 94 the base of transistor 100 becomes more positive causing transistor 100 to begin conducting and allowing current to flow through the base-emitter junctions of transistors 110, 112. Resistors 122, 124 are provided to limit the degree of current unbalance which may be provided by the potentiometer 114.

The collectors of transistors 110, 112 are connected to respective right and left terminals 126, 128 of output jack 130 through current sensing resistors 132, 134 and blocking diodes 136, 138, respectively. The amplitudes of the currents through terminals 126, 128 are proportional to the base currents of transistors 110, 112 which are controlled by the position of the wipers for potentiometers 96, 114. Current sensing resistors 132, 134 are selected so that the voltage drop across them at a preset maximum current is equal to the trigger voltage of thyristors 140, 142 which shunt the current from transistors 110, 112 respectively to ground in an overcurrent condition.

The output of inverter 70 is also applied to a lamp driver circuit 146 for enabling the indicator lamps. The trailing edge of the positive going pulse at the output of inverter 70 is differentiated by capacitor 148 and resistor 150 to produce a positive going pulse at the output of inverter 152 which saturates transistor 154 through resistor 156. A capacitor 158 is positioned between the collector of transistor 154 and input of inverter 152 to increase the transient response of the switching circuit. As transistor 154 saturates its collector is effectively switched to the negative voltage supply for driving various lamp circuits. The transistor 154 is normally held at cutoff by resistor 160 extending between the base and emitter of transistor 154.

In the pulse mode switch 162 is closed thereby connecting the emitter of transistor 164 to ground and allowing current to flow from the collector of transistor 164 through zener diode 166, potentiometer 168 and resistor 170. The wiper of potentiometer 168 is set so that normal battery voltage is sufficient to allow transistor 164 to conduct causing current to flow through resistor 172 and LED 36 (FIG. 2) to indicate that the battery voltage is sufficient. When the battery voltage falls to a level slightly greater than the reverse breakdown voltage of zener diode 166 transistor 164 is driven to cutoff thereby forward biasing the base-emitter junction of transistor 174 to allow current to flow through resistor 176 and the parallel combination of resistor 178 and light emitting diode 38 which indicates that the battery should be replaced.

In the test mode a constant voltage is applied to the resistors 190, 194, and the currents in the electrode circuits are measured to detect for open circuit and unbalanced resistance conditions. In the "test" mode switch 180 is closed thereby allowing current to flow through zener diode 182, diode 184 and resistors 186, 188. Consequently, the cathode of diode 184 is placed at a preset negative voltage equal to the reverse breakdown voltage of the zener diode 182 plus the voltage drop across diode 184. This reference voltage is applied to terminals 126, 128 through respective series circuits of resistor 190 and diode 192 and resistor 194 and diode 196. Diodes 192, 196 are normally back biased when a pulse is produced in the pulse mode so that the test circuit does not interfere with the operation of the stimulator. The reference voltage on the anode of zener diode 182 is applied directly to the non-inverting terminals of operational amplifiers 198–204. The reference voltage is then compared to the voltage across resistor 190 and diode 184 by operational amplifiers 198 and 204, and the reference voltage is compared to the voltage across resistor 194 and diode 184 by operational amplifiers 200, 202. Under open circuit conditions the reference voltage is less negative than the voltages at the cathodes of diodes 192, 196 by approximately the voltage drop across diode 184. Consequently, the output of operational amplifiers 200, 204, which function as comparators, is positive thereby causing current to flow through light emitting diode 30b and resistor 210 and light emitting diode 30a and resistor 212 to indicate an open circuit condition. When the currents through resistors 190, 194 produce voltage drops across resistors 190, 194 greater than the voltage drop across diode 184 the outputs of operational amplifiers 200, 204 become negative thereby terminating current flow through light emitting diodes 30a, b. Operational amplifiers 198, 202 function as amplifiers since their outputs are connected to their inverting inputs by resistors 214, 216, respectively. The output of operational amplifier 198 is proporational to the current through resistor 190, and thus proportional to the conductance of the right electrode circuit. Similarly, the voltage at the output of operational amplifier 202 is proportional to the current through resistor 194 and thus proportional to the conductance of the left electrode circuit. These output voltages are compared to each other as described hereinafter to indicate an unbalanced condition in which the current through one resistor 190, 194 exceeds the current through the other resistor 190, 194 by a predetermined value. The output of operational amplifier 198 is connected to the base of transistor 218 through resistor 220, and the output of operational amplifier 202 is connected to the emitter of transistor 218 Consequently, when the output of operational amplifier 198 is more negative than the output of operational amplifier 202 by the voltage across a forwardly biased diode, transistor 218 begins conducting thereby saturating transistor 222 through resistor 224 and allowing current to flow through resistor 228 and left conductance low light emitting diode 34b. The base of transistor 222 is connected to the lamp drive output line for lamp 30b through transistor 230 which is saturated through resistor 232 responsive to an open circuit indication at the output of operational amplifier 200. Thus current is unable to flow through indicator lamp 34b when indicator lamp 30b is illuminated. The low conductance indicator 34b for the right electrode circuit operates in essentially the same manner. The output of operational amplifier 202 is connected to the base of transistor 234 through resistor 236, and the output of operational amplifier 198 is connected to the emitter of transistor 234 so that transistor 234 is saturated when the output of operational amplifier 198 is less negative than the output of operational amplifier 202 by the voltage across a forwardly biased diode. As transistor 234 conducts, transistor 238 becomes saturated through resistor 240 to allow current flow through resistor 228 and light emitting diode 34a. Transistor 243 is saturated through resistor 242 by an open right electrode circuit indication at the output of operational amplifier 204.

The open circuit indications from the output of operational amplifiers 200, 204 are applied to the base of transistor 244 through resistor 247 and diodes 248, 250, respectively. Transistor 244 then saturates thereby back biasing the base-emitter junction of transistor 252. However, when neither of the operational amplifiers 200, 204 are producing an open circuit indication, transistor 244 is held at cutoff by resistor 254 extending between the base and emitter of transistor 244 so that the voltage selected by resistors 246, 249 is placed on the base of transistor 252 to allow current to flow through light emitting diode 32. When either of the low conductance indicator lamps 34 are illuminated the voltage drop across resistor 228 causes the voltage on the base of transistor 252 to drop sufficiently to back bias the base-emitter junction of transistor 252 to prevent the LED 32 from illuminating. If none of the lamps 30, 34 are illuminated, then good indicating lamp 32 flashes each pulse.

We claim:

1. A mandible stimulator for providing controlled electrical stimulation of the multiplicity of muscles innervated by the fifth and seventh cranial nerves, comprising:
   a power source;
   output means having right, left and common outputs, said output means including a right electrode connected to said right output, a left electrode connected to said left output and a dispersal electrode connected to said common output, said output means being adapted to form a right electrode circuit through the body of a patient between the right side of said patient's face and said dispersal electrode and a left electrode circuit through the body of said patient between the left side of said patient's face and said dispersal electrode;
   amplitude control means for selecting the intensity of said electrical stimulation;
   constant current pulsing means connected to said power source for periodically generating a right stimulus pulse between said right and common outputs, and a left stimulus pulse between said left and common outputs, said right and left stimulus pulses producing currents in said right and left electrode circuits, respectively, which are a constant value corresponding to the intensity selected by said amplitude control means such that the electrical stimulation of said muscles is unaffected by variations in electrode circuit resistance; and
   electrode circuit testing means for measuring the conductance of said electrode circuits and providing a visual indication of the condition thereof, said testing means comprising right and left circuit conductance sensing means for generating right and left conductance signals indicative of the conductance in said right and left electrode circuits, respectively;
   first comparator mens receiving said right and left conductance signals for illuminating a right open circuit indicating lamp and a left open circuit indicating lamp responsive to the conductance in said right and left electrode circuits, respectively, being less than a first predetermined value; and
   second comparator means receiving said right and left conductance signals for illuminating a right circuit low conductance indicating lamp responsive to the conductance of said right electrode circuit being less than the conductance of said left electrode circuit by a second predetermined value, and for illuminating a left circuit low conductance indicating lamp responsive to the conductance of said left electrode circuit being less than the conductance of said right electrode circuit by said second predetermined value thereby providing a visual indication of circuit unbalance.

2. The mandible stimulator of claim 1 further including low conductance indicating lamp inhibit means for preventing said low conductance indicating lamps from illuminating when the respective open circuit indicating lamp is illuminated such that a visual indication of electrode circuit low conductance is not produced when said electrode circuit is open.

3. The mandible stimulator of claim 1 further including indicator means receiving said right and left conductance signals for illuminating a good circuit condition indicating lamp responsive to the conductance of said right electrode circuit and the conductance of said left electrode circuit exceeding said first predetermined value.

4. A mandible stimulator for providing controlled electrical stimulation of the multiplicity of muscles innervated by the fifth and seventh cranial nerves, comprising:
   a power source;
   output means having right, left and common outputs, said output means including a right electrode connected to said right output, a left electrode connected to said left output and a dispersal electrode connected to said common output, said output means being adapted to form a right electrode circuit through the body of a patient between the right side of said patient's face and said dispersal electrode and a left electrode circuit through the body of said patient between the left side of said patient's face and said dispersal electrode;
   amplitude control means for selecting the intensity of said electrical stimulation, said amplitude control means including potentiometer means having a linear resistance winding and potentiometer wiper adjustably contacting said resistance winding, control circuit means connected to said potentiometer means, said control circuit means having a non-linear transfer function such that the intensity of said electrical stimulation is a non-linear function of the position of said potentiometer wiper and compensating means connected to said potentiometer means and said control circuit means for counteracting the non-linear characteristic of said control circuit means such that the intensity of said electrical stimulation is a linear function of the position of said potentiometer; and
   constant current pulsing means connected to said power source for periodically generating a right stimulus pulse between said right and common outputs, and a left stimulus pulse between said left and common outputs, said right and left stimulus pulses producing currents in said right and left electrode circuits, respectively, which are a constant value corresponding to the intensity selected by said amplitude control means such that the electrical stimulation of said muscles is unaffected by variations in electrode circuit resistance.

5. In a mandible stimulator for providing controlled electrical stimulation of the multiplicity of muscles innervated by the fifth and seventh cranial nerves, said stimulator further including a right electrode adapted to be secured to the right side of a patient's face, a left electrode adapted to be secured to the left side of said patient's face and a dispersal electrode adapted to be connected to an upper part of said patient's body thereby forming a right electrode circuit through the body of said patient between the right side of said patient's face and said dispersal electrode and a left electrode circuit through the body of said patient between the left side of said patient's face and said dispersal electrode, and means for applying said stimulation to said electrodes, the improvement comprising electrode circuit testing means for measuring the conductances of said electrode circuits and for providing a visual indication of the condition thereof, said testing means comprising:
   right and left circuit conductance sensing means for generating right and left conductance signals indicative of the conductance in said right and left electrode circuits, respectively;

first comparator means receiving said right and left conductance signals for illuminating a right open circuit indicating lamp and a left open circuit indicating lamp responsive to the conductance in said right and left electrode circuits, respectively, being less than a first predetermined value;

second comparator means receiving said right and left conductance signals for illuminating a right circuit low conductance indicating lamp responsive to the conductance of said right electrode circuit being less than the conductance of said left electrode circuit by a second predetermined value, and for illuminating a left circuit low conductance indicating lamp responsive to the conductance of said left electrode circuit being less than the conductance of said right electrode circuit by said second predetermined value thereby providing a visual indication of circuit unbalance.

6. The mandible stimulator of claim 5 further including low conductance indicating lamp inhibit means for preventing said low conductance indicating lamps from illuminating when the respective open circuit indicating lamp is illuminated such that a visual indication of electrode circuit low conductance is not produced when said electrode circuit is open.

7. The mandible stimulator of claim 5 further including indicator means receiving said right and left conductance signals for illuminating a good circuit condition indicating lamp responsive to the conductance of said right electrode circuit and the conductance of said left electrode circuit exceeding said first predetermined value.

* * * * *